United States Patent
Kuo et al.

(10) Patent No.: US 6,623,480 B1
(45) Date of Patent: Sep. 23, 2003

(54) FLEXIBLE RECORDING/HIGH ENERGY ELECTRODE CATHETER WITH ANCHOR FOR ABLATION OF ATRIAL FLUTTER BY RADIO FREQUENCY ENERGY

(75) Inventors: Chien-Suu Kuo, Lexington, KY (US); John C. Gurley, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/360,257

(22) Filed: Jul. 23, 1999

Related U.S. Application Data

(60) Provisional application No. 60/094,001, filed on Jul. 24, 1998.

(51) Int. Cl.[7] .............................................. A61B 18/18
(52) U.S. Cl. ......................... 606/41; 606/42; 607/101; 607/113
(58) Field of Search ...................... 606/41–49; 607/96, 607/98, 99, 101, 113, 115, 116, 119, 126, 127; 604/19, 508, 510

(56) References Cited

U.S. PATENT DOCUMENTS

| | | | |
|---|---|---|---|
| 4,998,975 A | * | 3/1991 | Cohen et al. .................. 607/5 |
| 5,106,386 A | * | 4/1992 | Isner ........................... 606/15 |
| 5,111,811 A | | 5/1992 | Smits |
| 5,279,299 A | | 1/1994 | Imran |
| 5,405,374 A | | 4/1995 | Stein |
| 5,473,812 A | | 12/1995 | Morris et al. |
| 5,476,502 A | | 12/1995 | Rubin |
| 5,507,802 A | | 4/1996 | Imran |
| 5,522,874 A | | 6/1996 | Gates |
| 5,575,787 A | * | 11/1996 | Abela et al. .................. 606/11 |
| 5,578,067 A | | 11/1996 | Ekwall et al. |
| 5,582,609 A | | 12/1996 | Swanson et al. |
| 5,673,695 A | | 10/1997 | McGee et al. |
| 5,876,398 A | * | 3/1999 | Mulier et al. ............... 128/898 |
| 6,026,567 A | * | 2/2000 | Swoyer et al. ................ 29/854 |
| 6,055,457 A | * | 4/2000 | Bonner ........................ 607/126 |

* cited by examiner

*Primary Examiner*—Rosiland S. Kearney
(74) *Attorney, Agent, or Firm*—King & Schickli, PLLC

(57) ABSTRACT

An electrode catheter is provided having a predetermined flexibility throughout the entire length or at least at the contact portion, such as the electrode region, to allow for the molding of the contact portion such that it conforms to the shape of the heart at a preselected desired target area, such as the isthmus between the inlet of inferior vena cava and posterior tricuspid annulus. The catheter also includes a guiding sheath that is preferably semirigid and may be pre-shaped with at least one bend or angulation to assist in molding to ensure that the electrode region overlies the desired target treatment area. A remotely controlled anchoring device is provided at the distal end of the catheter for anchoring it in position to facilitate the molding operation and placement over the target treatment area. A method of cardiac ablation using the catheter of the present invention is also disclosed.

18 Claims, 6 Drawing Sheets

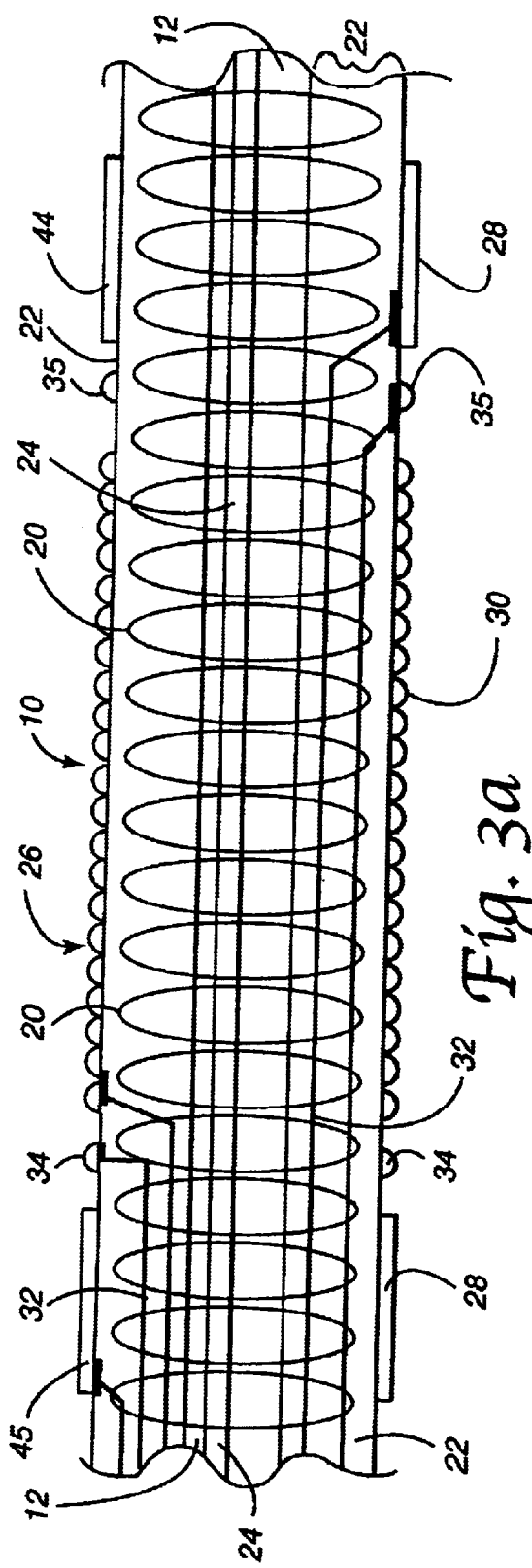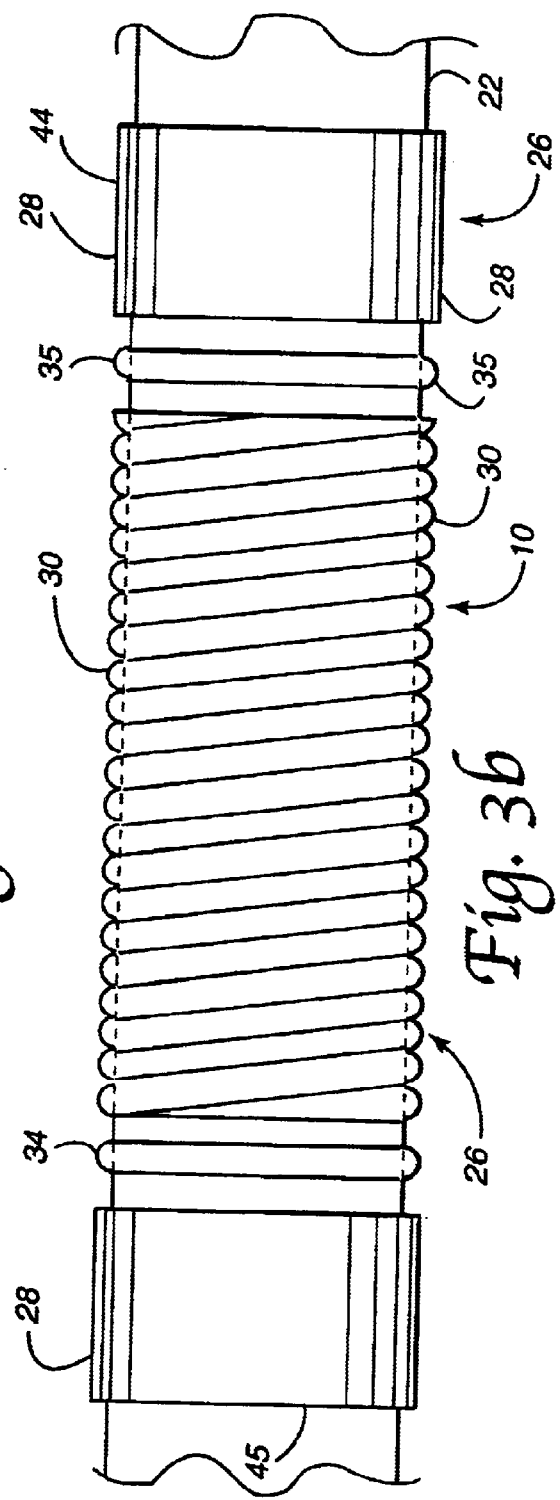

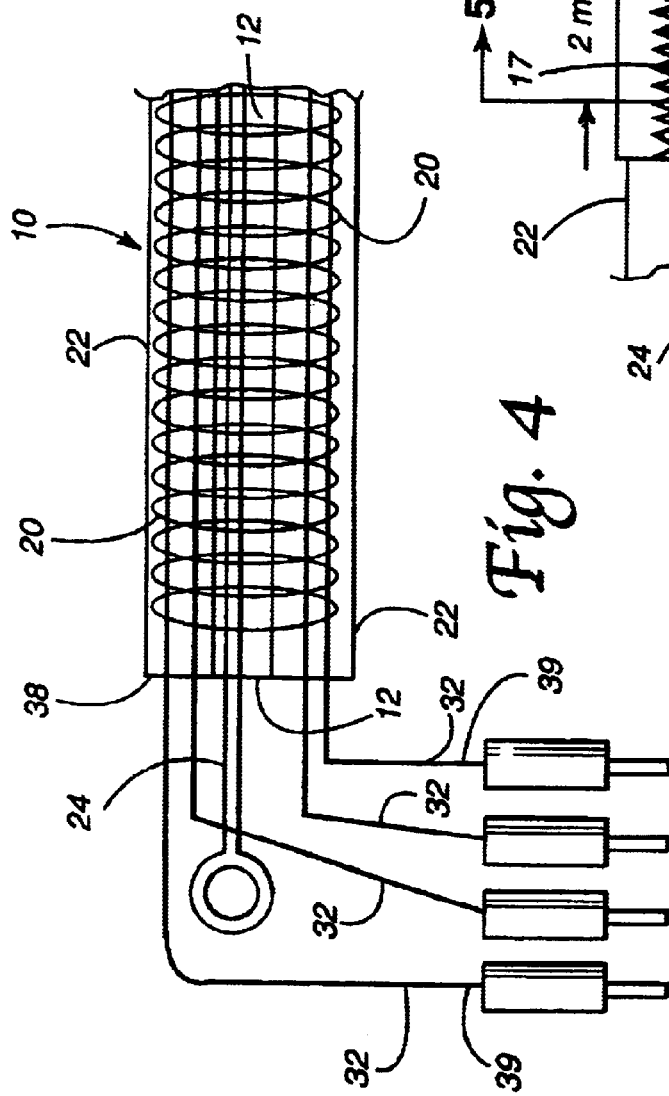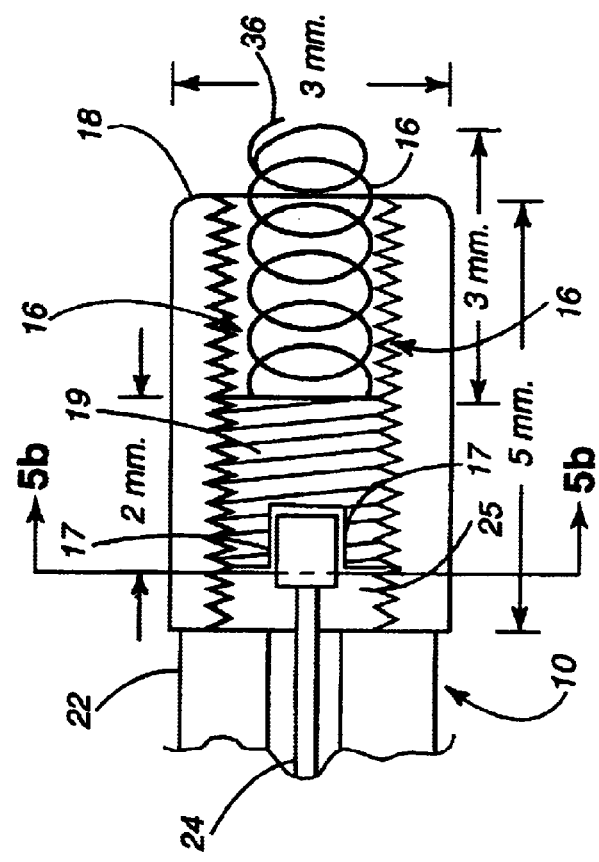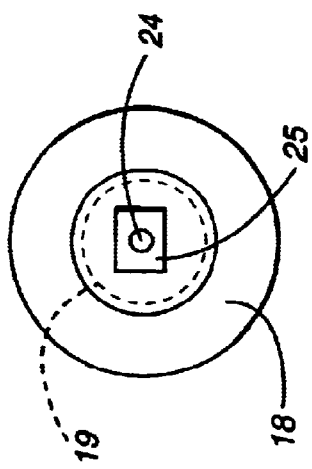

FLEXIBLE RECORDING/HIGH ENERGY ELECTRODE CATHETER WITH ANCHOR FOR ABLATION OF ATRIAL FLUTTER BY RADIO FREQUENCY ENERGY

This application claims priority from U.S. Provisional Patent Application Ser. No. 60/094,001, filed Jul. 24, 1998.

TECHNICAL FIELD

The present invention relates to the field of interventional cardiology and, more particularly, to a catheter and a related method for the ablation of atrial flutter utilizing radio frequency energy.

BACKGROUND OF THE INVENTION

Many advances have been made in interventional therapy for cardiac arrhythmias, as devices such as catheters for mapping and ablation of target areas have improved. Many arrhythmias are now frequently treated by using specially adapted radio frequency (RF) catheters. The successful treatment rate of RF catheters may reach >90% for certain cardiac arrhythmias. Moreover, RF ablation using a catheter does not require general anesthesia and recovery from the procedure is rapid.

Electrical conduction problems such as ventricular tachycardia and artioventricular node reentrant tachycardia are also routinely treated without general anesthesia utilizing radio frequency ablation. However, for those patients in whom maintenance of sinus rhythm is not possible (approximately 20% of patients over 60 years old), control of ventricular rate is achieved with AV nodal blockers such as digoxin, β-blockers, or calcium channel blockers. Although prior to the present invention, a "cure" of atrial fibrillation with catheter ablation techniques appeared not to be possible, various attempts had been made at permanent modification of the AV conduction such that rapid conduction could be eliminated, but normal conduction (fewer than 100 beats per minute) remains, thereby avoiding the need for a permanent pacemaker. Unfortunately, these attempts have been unsuccessful. See, Vogel & King, The Practice of Interventional Cardiology, $2^{nd}$ Ed., pages 671–683 (1993).

Accordingly, specially adapted radio frequency ablation catheters designed for either general purpose or specific application are known in the art, some of which are widely used. For example, U.S. Pat. No. 5,507,802 to Irman, for "METHOD OF MAPPING AND/OR ABLATION USING A CATHETER HAVING A TIP WITH FIXATION MEANS." (Irman '802) generally discloses a mapping and/or ablation catheter 11 having a flexible elongate tubular member 12, with a large central lumen 16 and a plurality of additional lumens 17 (see, column 2, lines 7–35). Anchoring or fixation means are carried by the distal tip 21 with means for selective engagement and disengagement of the fixation means. Irman '802 also discloses plural ring platinum electrodes 46, 47 near the distal tip and conducting means 48, 49 which extend through the additional lumens of the catheter for connection to a remote source of radio frequency energy (see, column 3, lines 14–20).

U.S. Pat. No. 5,673,695 to McGee et al. for "METHODS FOR LOCATING AND ABLATING ACCESSORY PATHWAYS IN THE HEART" (McGee et al. '695) discloses an ablation catheter having a multifunction element 40 (ring electrodes E1–E10) spaced apart and located near the distal tip for location/ablation of accessory electrical pathways of the heart (see, column 6, lines 7–52). The body 42 of the catheter can be constructed from a variety of flexible resilient materials and also may include an inner core of a suitable metal or super elastic material such as Nitinol® (see, column 5, lines 48–67).

U.S. Pat. No. 5,582,609 to Swanson et al., for "SYSTEMS AND METHODS FOR FORMING LARGE LESIONS IN BODY TISSUE USING CURVILINEAR ELEMENTS" (Swanson et al. '609) describes generally the need for catheters designed especially for treatment of atrial fibrillation and atrial flutter, having "the larger ablating mass required for these electrodes among separate multiple electrodes spaced apart along a flexible body" (see, column 1, lines 42–61). The '609 reference discloses both spaced apart ring electrodes and coiled spring configurations (see, FIGS. 36, and columns 6–7) and at column 8, lines 23–31 further describes the use of a sliding sheath 50 (FIG. 12). However, this sheath 50 slides within the lumen of catheter body 12 and is used to vary the impedance and the surface area contact of the coil electrode 46. The '609 reference specifically discloses the lesion patterns attainable with the device for treatment of atrial flutter and discloses how lesion characteristics can be controlled (see, column 9, lines 5–30).

U.S. Pat. No. 5,111,811 to Smits, for "CARDIOVERSION AND DEFRIBRILLATION LEAD SYSTEM WITH ELECTRODE EXTENSION INTO THE CORONARY SINUS AND GREAT VEIN." discloses a screw anchor fixation assembly 76 having a rotatable corkscrew electrode 78 (see, FIG. 4 and column 6, lines 33–44.

U.S. Pat. No. 5,578,067 to Elkwall et al., for "MEDICAL ELECTRODE SYSTEM HAVING A SLEEVE.BODY AND CONTROL ELEMENT THEREFOR FOR SELECTIVELY POSITIONING AN EXPOSED CONDUCTOR AREA" discloses a sleeve like body 19 (sheath) having a window-like opening 18. The sheath 19 slides along the electrode cable 3 to vary the location of the exposed electrode 6a (see, FIG. 4, and column 5, lines 28–45).

Atrial flutter is a rapid abnormal rhythm of the atrium with the electrical impulse traveling around the orifice of the right atrium at the junction with the inferior vena cava, the major vein collecting blood from the lower body and returning it to the heart. This abnormal electrical impulse travels through a strip of heart muscle, termed the isthmus, located between this orifice and another orifice between the right atrium and right ventricle.

A total interruption of this pathway, i.e. the isthmus, by an interventional procedure such as RF ablation has been shown play a key role in successfully curing atrial flutter. The current technique utilizes a general purpose RF ablation catheter. The tip of the catheter is dragged across the entire width of the isthmus under fluoroscopic guidance to create a complete linear cut by RF energy. Using this technique requires a high skill level and may necessitate multiple attempts to achieve a proper cut. Thus, the procedure may be time consuming and result in heavy X-ray exposure. Furthermore, its availability is limited to selected major medical centers having a large patient population.

As should be appreciated, creation of a consistent and complete linear lesion requires full and stable contact between the electrode and the endocardial surface along the entire length of the cut. Currently available catheters including those described in the above-cited patents lack the ability to maintain such contact without either dragging the catheter or repositioning it several times during the procedure. Therefore, the procedure remains time consuming and highly dependent on the operator's skill level.

Accordingly, a need is identified for a radio frequency ablation catheter that is specially adapted for the treatment of atrial flutter that makes the treatment less time consuming and less dependent on the operator's skill. The catheter would be flexible to facilitate the bending necessary to place the electrodes used for ablation over the target area for treatment. Anchoring means would also be included to anchor the catheter in position to facilitate the bending operation and to ensure that the catheter remains in the proper position over the target area during the procedure, thereby avoiding the need for dragging or repositioning of the catheter during the procedure. Overall, such a catheter would be simpler to operate and thus require a lower skill level to successfully perform the ablation procedure.

OBJECTS OF THE INVENTION

It is a primary object of the present invention to provide a radio frequency ablation catheter and a related method of catheterization that overcomes the limitations and shortcomings of the above-referenced prior art devices and methods.

It is another object of the present invention to provide a radio frequency ablation catheter specially adapted for the treatment of atrial flutter that is simpler to operate, thereby making a successful outcome less dependent upon the skill of the operator.

Another object of the invention is to provide a catheter electrode for the purpose of ablative procedures using radio frequency energy that is more flexible than those presently available.

Yet another object of the invention is to provide an anchoring device at the distal end of the catheter to ensure that stable contact with the target cardiac tissue is maintained.

A further object of the invention is to provide a catheter wherein the ablation electrodes are positioned in the middle portion of the catheter, rather than at the distal end, said electrodes including multiple closely spaced ring electrodes or a long spring coil electrode for creating a linear lesion along the entire length of the cut line, i.e., over the entire isthmus.

It is also an object of the invention to provide a pre-shaped semi-rigid guiding sheath to assist in molding the contact portion of the catheter.

A further object of the invention is to provide a catheter having a removable stylet and corkscrew anchoring means coupled with a flexible electrode, shaft and a pre-molded sheath that is specific for ablative treatment of atrial flutter.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

SUMMARY OF THE INVENTION

To achieve the foregoing and other objects, and in accordance with the purposes of the present invention as described herein, an electrode catheter is provided having a predetermined flexibility throughout the entire length or at least at the contact portion, such as the electrode region. This flexibility advantageously allows for the molding of the contact portion such that it conforms to the shape of the heart at a preselected desired target area, such as the isthmus between the inlet of inferior vena cava and posterior tricuspid annulus. Moreover, the flexibility of the catheter allows the operator to maintain steady contact with the target area for delivering radio frequency energy, thereby reducing the operator skill level necessary for performing the ablation procedure.

In one embodiment, the device of the invention comprises either a flexible multipolar or monopolar electrode of a ring or spring coil configuration. These ablation electrodes are positioned in the middle portion of the catheter, i.e., away form the distal portion (as with currently available catheters), to ensure proper positioning over the target area (which as described below is primarily the cardiac isthmus). Preferably, the most distal portion of or ring forming the electrode is mounted approximately 10 cm from the end of a hollow tube catheter having a sealed distal end. Advantageously, the spaced ring or spring coil electrode configurations work in conjunction with the flexible tubular body to allow the catheter to freely bend. While the catheter body is made of flexible material that resists a predetermined amount of tension, it is in general is not freely stretchable. The catheter body is also electrically insulating and is preferably constructed from a biocompatable material, such as polytetrafluoroethylene (PTFE), that is non-thrombogenic and can resist sustained heat of up to 100° C.

The ring or spring coil electrodes are attached to at least one electric wire running through the lumen of catheter. Alternatively, the electric wire can be mounted within the body of the catheter and exteriorized at the proximal end for electrical connection to a recorder and a radiofrequency energy generator. The resistance of the connecting wires should be low enough to allow delivery of the energy up to 50 watts (or higher if such higher energy generator is approved by FDA) without creating heat or breaking insulation.

In accordance with an important aspect of the invention, a screw-in anchoring device or anchoring hook is located at the distal tip of the catheter. This device includes a corkscrew tip that is used to anchor the catheter at a preselected location during deployment, which advantageously allows the operator to bend or mold the catheter as necessary to place the electrodes at the desired target location.

Inside the catheter body is a lumen sized to accommodate a'stylet. The stylet provides some rigidity to the catheter during manipulation and deployment, which is similar to the technique used for implantation of a pacemaker electrode. In one embodiment, the stylet is configured with a means for remotely controlling the anchoring device provided at the distal tip of the electrode catheter. By using the stylet to control the anchoring device, removal or re-insertion of the catheter at any time during an ablation procedure is possible, as may be necessary for use in particular circumstances.

The hollow tube-like member forming the catheter body is preferably supported by a metallic spring coil to maintain the desired flexibility. In addition to providing support, this spring coil aids in supporting and reduces the incidence of kinking without sacrificing flexibility. The spring coil is preferably embedded in the wall of the catheter.

In accordance with another important aspect of the present invention, a guiding sheath is provided to assist in molding the electrode portion of the catheter over the isthmus during deployment. The sheath is preferably semi-rigid and pre-shaped with a bend or angulation. As described further below, the sheath fits over the catheter and allows it to be molded in vivo to ensure that stable contact is made with the target treatment area.

As should be appreciated, the catheter of the present invention is designed primarily for use in radio frequency ablation procedures performed at the isthmus between the inlet of inferior vena cava and posterior tricuspid annulus for permanent treatment of atrial flutter in human subjects. More particularly, the objective of the specially designed devices described herein is to increase the ease of use of the catheter in performing such a procedure while achieving a high success rate. For instance, using the presently proposed catheter, manipulation/positioning of the catheter during its deployment is much less dependant on the skill and dexterity of the operator because of the combined function of the anchoring device and preshaped guiding sheath. Therefore, the time required to complete the ablation procedure and the concomitant X-ray exposure is much less than that associated with conventional ablation devices, yet the high success rate of the procedure is maintained even in the clinical electrophysiology laboratory of an average size.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming apart of the specification illustrate several aspects of the present invention and, together with the description, serves to explain the principles of the invention. In the drawings:

FIG. 3a is a cross-sectional view of an alternate embodiment of the ring electrode segment of the catheter of the invention;

FIG. 3b is a side view of the alternate embodiment shown in FIG. 3a;

FIG. 4 shows the proximal end of the catheter shown in FIG. 1 further showing the exteriorization of four conducting wires and the open central lumen of the catheter for insertion of the stylet;

FIG. 5a shows the distal end of the catheter and the anchoring device;

FIG. 5b is a cross-sectional view of the distal end of the catheter and the anchoring device taking along line 5b—5b.

DETAILED DESCRIPTION OF THE INVENTION

Figure 1:
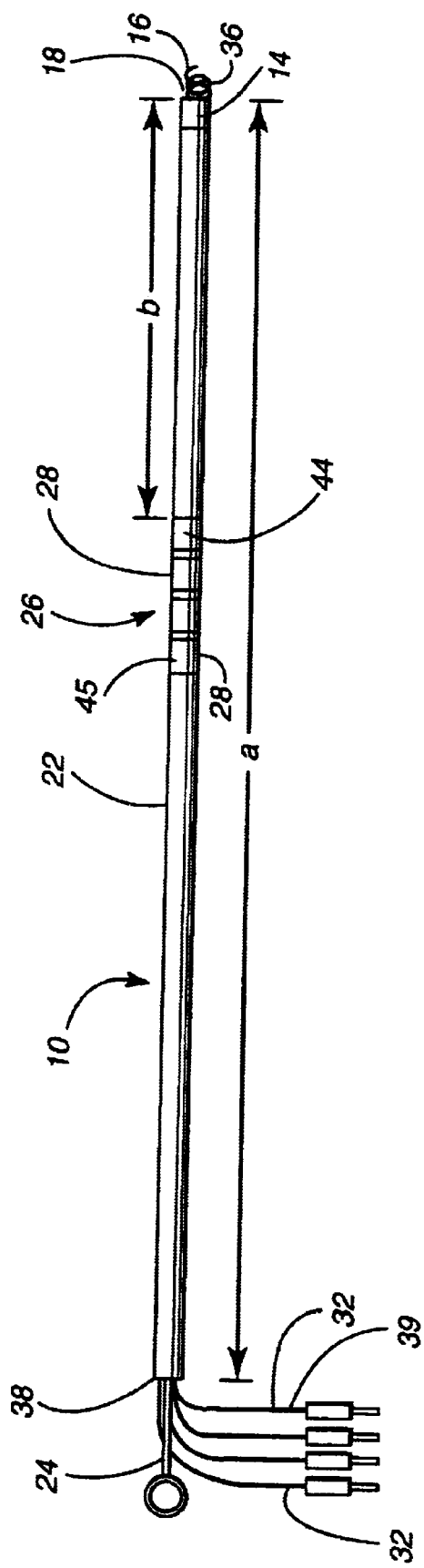
FIG. 1 is a top plan view of the device of the present invention.

In general, the concept of the present invention is to provide: (1) a catheter electrode that is more flexible than currently available catheters and is specially adapted for the ablative treatment of atrial flutter utilizing radio frequency energy; (2) a distally located anchoring device at the tip of the catheter which can be controlled remotely by the surgeon/operator; (3) ablation electrodes that are positioned in the middle portion of the catheter, i.e., away form the distal portion (as with currently available catheters); (4) multiple closely spaced electrodes or a single long spring coil electrode for linear lesion creation; and (5) a pre-shaped semi-rigid guiding sheath to assist molding of the contact portion of the catheter.

In particular, the present invention, as shown in FIGS. 1–5, is directed to a device for the treatment of a specific cardiac anomaly, i.e., atrial flutter. In one embodiment, the device is a small (approximately 3 mm O.D.) highly flexible catheter 10 approximately 100 cm in length. A central lumen 12 of approximately 1 mm I.D. extends through the catheter 10. The catheter 10 has a sealed tip 14 with an anchoring device 16, such as a cork screw tip, located at the distal end 18. A metallic spring coil 20 may be embedded in the wall 22 of the catheter 10 to aid in support and reduce the incidence of kinking without sacrificing flexibility. A semi-rigid stylet 24 sized complimentary to the catheter lumen 12 and having means for engaging and controlling the anchoring device 16 is included.

The catheter 10 also includes an electrode portion 26. In the preferred embodiment, the electrode portion 26 of the catheter 10 includes flexible, multiple ring electrodes 28 (or alternatively coiled spring electrode 30 interspersed between two ring electrodes 44,45, preferably made of platinum) for the transmission of radio frequency energy. These ring electrodes 28 are located a predetermined distance (approximately 8–10 cm) from the distal end 18 of the catheter .10 and are preferably formed of platinum. The total length (shown as segment a, FIG. 1) should be long enough to place the distal tip 18 of the catheter 10 at the right ventricular apex from either the right or left femoral vein entry. As should be appreciated, this length can vary with the patient, but generally is estimated to be approximately 100 cm. The length of segment b, the distance form the electrode portion 26 to the distal end 18, can vary between about 6 cm and about 16 cm but is preferably about 8–10 cm. This distance of segment b can be accurately determined by a echocardiogram for a selected patient and the appropriately spaced catheter selected for a particular ablative procedure.

Each ring 28 of the electrode portion 26 is preferably connected to an external radio frequency energy source by a separate insulated conducting wire 32. The conducting wire 32 preferably maintains a high flexibility and low resistance to allow for the passage of electrical energy of up to about 50 watts for the multiple ring electrode 28 or up to about 100 watts for the coil spring 30 embodiment. As described in detail further below, the number and spacing of the multiple rings 28 of the electrode portion 26 can be varied to adjust the flexibility of the catheter 10 to assure proper molding and contour of the electrode portion 26 for stable contact with the endocardial surface at the isthmus 50.

In the spring coil 30 embodiment, as illustrated in FIGS. 3a, 3b and 4, isolated ring electrodes 34,35 are located between a ring electrode 28 and the coil spring electrode 30. These electrodes 34, 35 may be utilized for bipolar recording to aid in positioning by defining the isthmus 50 boundary via the electrical signal.

The flexibility of the catheter body 22 allows the molding of the electrode portion 26 of the catheter 10 by a relatively simple manipulation from a remote, or proximal, end 38 outside patient's body. An anchoring device 16 at the distal end (tip) 18 of the catheter 10 is provided to secure an anchoring point at a preselected location such as inside the right ventricle (e.g., the apical region). This allows for the pulling of the catheter 10 from the proximal end 38, yet assures that stability is achieved and contact of the electrode portion 26 of the catheter 10 with the endocardial surface of the target site is made. In this embodiment, the contact or body portion containing the electrodes must be very flexible for molding.

In the preferred embodiment, the semi-rigid guiding sheath 40 is supplied to assist in molding the electrode portion 26 over the isthmus during deployment and to maintain the proximal end of the electrode portion 26 in contact with the endocardial surface 60. The guiding sheath 40 is formed of a semi-rigid material and is pre-shaped to conform to the size and shape of the isthmus 50. More particularly, as illustrated in FIG. 6b, the sheath 40 can be pre-shaped with at least one bend 41 or angulation such it can be utilized to apply a force to the forward wall of the IVC 62 such that the bend 41 rests against the rearward wall 47 of the IVC 62 and the electrode portion 26 is stabilized and held in firm contact with the isthmus 50. Alternatively, the sheath 40 can be made to be steerable such that the shape of the sheath can be changed in vivo to maintain the desired contact.

Also in the preferred embodiment, the catheter 10 includes a small caliber (approximately 3 mm, 9F size) highly flexible body with a central lumen 12 (approximately 1 mm diameter) and an anchoring device 16 at the distal end (tip) 18. The anchoring device 16 can be controlled from the proximal end 38 (i.e., outside the human body) for engagement and disengagement. One of skill in the art will appreciate that the size of the catheter 10 can vary with the size of the patient being treated but will generally range from about 4F outside diameter to about 9F, while the lumen 12 can range from about 0.08 mm to about 1.5 mm inside diameter.

Figure 2:
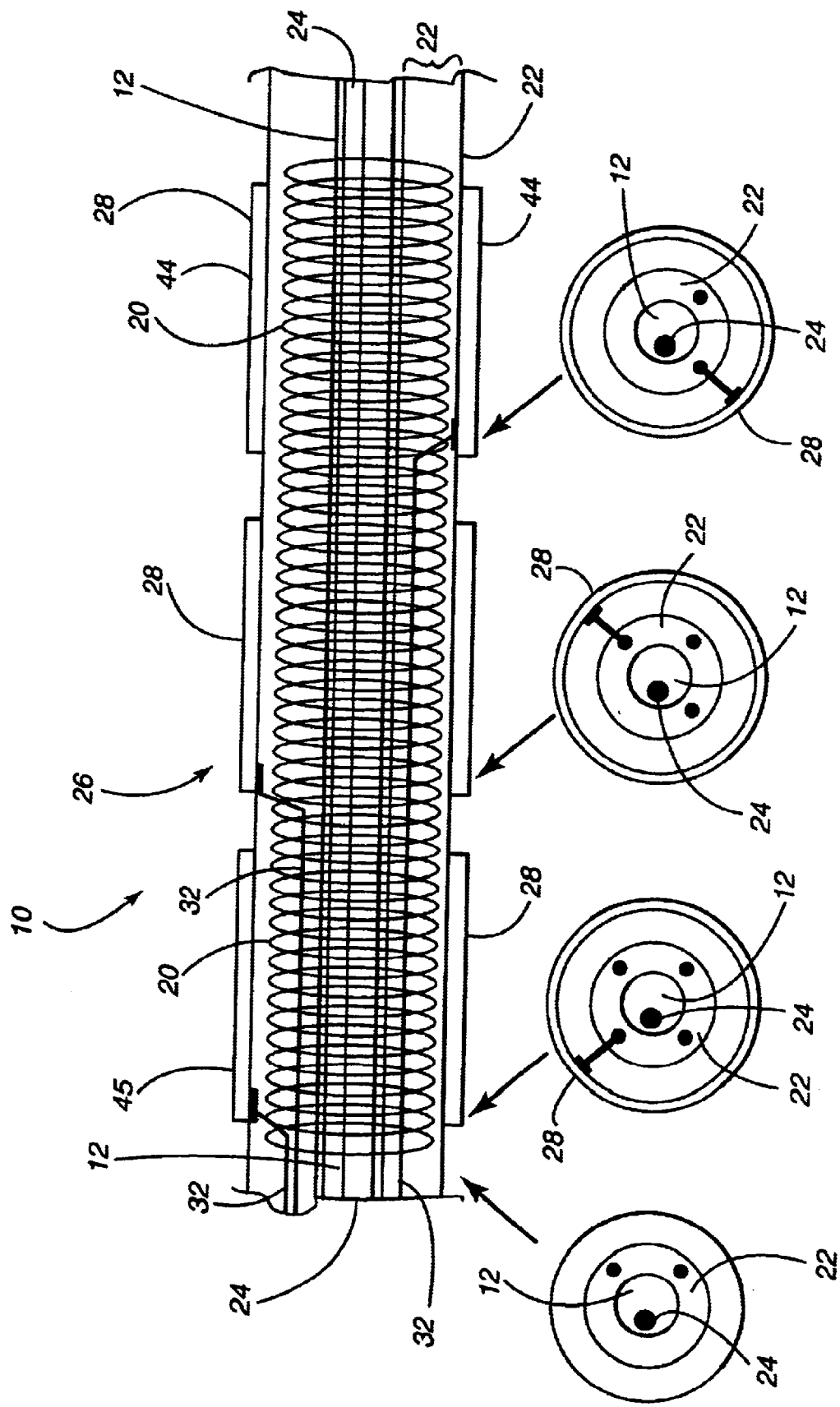
FIG. 2 is an enlarged longitudinal cross-sectional view of the ring electrode segment (the contact portion of the catheter electrode) shown in FIG. 1.

Referring now to FIGS. 1 and 2, the central lumen 12 is preferably sealed at.the distal end 18 or tip 14. At a predetermined distance from tip (b segment in FIG. 1), the multiple rings 28 are wrapped around the external surface 42 of the catheter 10. A small spacing is provided between each ring 28 to allow adjacent rings to move toward or away from each other during flexing of the catheter 10. This also ensures that the segment of the electrode portion 26 with ring electrodes 28 is sufficiently flexible to allow molding of this segment via the pre-shaped sheath 40 to maintain stable contact of the surface of ring electrodes 28 with the endocardial surface of the isthmus 50 of the right atrium between the inlet of inferior vena cava and posterior tricuspid annulus 46. During deployment, the most distal ring 44 is placed at the posterior tricuspid annulus 46.

The number of rings 28 is variable and can range from about 4 rings to about 8. The important consideration is that the span of the segments carrying the ring electrodes 28 should cover the entire width of the isthmus 50, but should not extend too far into the inferior vena cava 62 to minimize the risk of complication by perforation. The width of each ring 28 is preferably about 4 mm in the presently preferred embodiment, but a range of about 2 to 6 mm is possible. The spacing between each ring 28 can vary depending on the size of the patient, but is generally between about 1 mm and 2 mm. Of course, the number of the rings 28 and their the width and spacing is determined by the flexibility needed to allow the electrode portion 26 to be molded to the contour of the isthmus 50 in order to maintain stable contact between each ring electrode 28 and the endocardial surface of the isthmus 50.

As noted above, each ring 28 is connected electrically by a conducting wire 32 having high flexibility and very low resistance to allow passage of electrical energy up to 50 watts (or higher, up to a 100 watts or more for a large surface electrode, such as spring coil electrode 30) without creating excessive heat. Conducting wires 32 can be selected from any biocompatable metal having the above properties. However, the presently preferred metal is platinum. The conducting wires 32 connected to the ring electrode 28 run through the wall 22 of the catheter 10. The cross-sectional view of each ring 28 and the catheter 10 adjacent to the most proximal ring 45 depicts one of the possible locations of the conducting wires 32. The location of the conducting wires 32 (as observed from the cross-sectional view) is variable to provide the best flexibility of the electrode portion 26.

As should be appreciated by the skilled artisan, the conducting wire 32 may pass through the inside of the catheter, i.e., through the lumen 12, or it may be embedded within the wall 22 of the catheter body. Each conducting wire 32 is electrically insulated from other wires and configured such that the proximal end 39 is exteriorized for connecting to the interface of a recorder or a radio frequency energy generator.

Referring now to FIG. 2, the metallic spring coil 20 gives support to the catheter 10 and prevents it from collapsing into the central lumen 12 or kinking, yet the flexibility of the catheter 10 is retained. Preferably, the coil 20 is formed of stainless steel and is embedded in the wall 22 of the catheter 10.

Referring now to FIGS. 3a and 3b, the rings 28 located in the electrode portion 26 of the alternate embodiment shown (compare to FIG. 2) are replaced by a long segment of spring coil electrode 30. This may in certain circumstances provide more flexibility as compared to the version depicted in FIG. 2. However, the longer segment will increase the surface area of the electrode portion 26 which may require a higher energy (above 50 watts) radio frequency generator to achieve an adequate tissue temperature for creation of a coagulation lesion. An isolated single coil ring electrode 34,35 located between the ring electrode 28 and spring coil electrode 30 is utilized to provide a distal and a proximal bipolar recording site to aid in defining the boundary of the isthmus 50 by electrical signal. This mapping information can be used to guide the proper positioning of the catheter 10. The two ring electrodes 44,45 located at each end of the electrode portion 26 may also be used to deliver the radio frequency energy to extend the length of the lesion in the situation when both ends of the electrode portion are right at the boundary of the isthmus 50. This assures formation of a complete linear lesion across the entire width of the isthmus 50.

A semi-rigid stylet 24 is provided for placement inside the lumen 12 of the catheter 10. The stylet 24 provides additional rigidity during the introduction of the catheter 10 through a peripheral vein (right or left femoral vein) and for advancement to the right ventricular cavity. Moreover, in the preferred embodiment, the stylet 24 works in conjunction with means for remotely controlling the anchoring device 16 or screw-in anchor device (hook) 36 located at the distal end 18 of the catheter 10. For example, the distal tip 25 of the stylet 24 in the embodiment shown in FIGS. 5a and 5b is configured with a fitting (e.g., a male end or a bayonet fitting) that is complimentary to a fitting on the proximal end 17 of the anchoring device 16 such that engagement of the stylet 24 with the anchoring device 16 provides a means for remote control of the tip or hook 36 for engagement and disengagement. The fitting on the anchoring device 16 may be a square or hexagonal socket to correspond to the fitting at the distal end 25 of the stylet 24 (see cross-sectional view in FIG. 5b). As should be appreciated, the stylet 24 may be removed once the anchoring device 16 is secured and the catheter 10 is in proper position. The stylet 24 may also be re-inserted when desired to disengage the anchoring device 16 for removal of the catheter 10 at the end of the procedure.

Referring to FIG. 5a, the anchoring device 16 is preferably made of metal. However, other materials, such as plastic, can be employed. The anchoring device 16 also includes a central screw 19 that is controlled by the stylet 24 when engaged to move the corkscrew tip of the anchoring device 16 into position. The other end of the screw 19 is attached with a spiral hook 36. Thus, by turning the stylet 24 in a first direction, the central screw 19 moves forward toward the distal end 18, thereby anchoring the spiral hook 36 into the myocardium. Reverse turning the stylet 24 in the opposite direction retracts the central screw 19 toward the proximal end 17 of the anchoring device 16, releasing the spiral hook 36 from the myocardium.

Figure 6A:
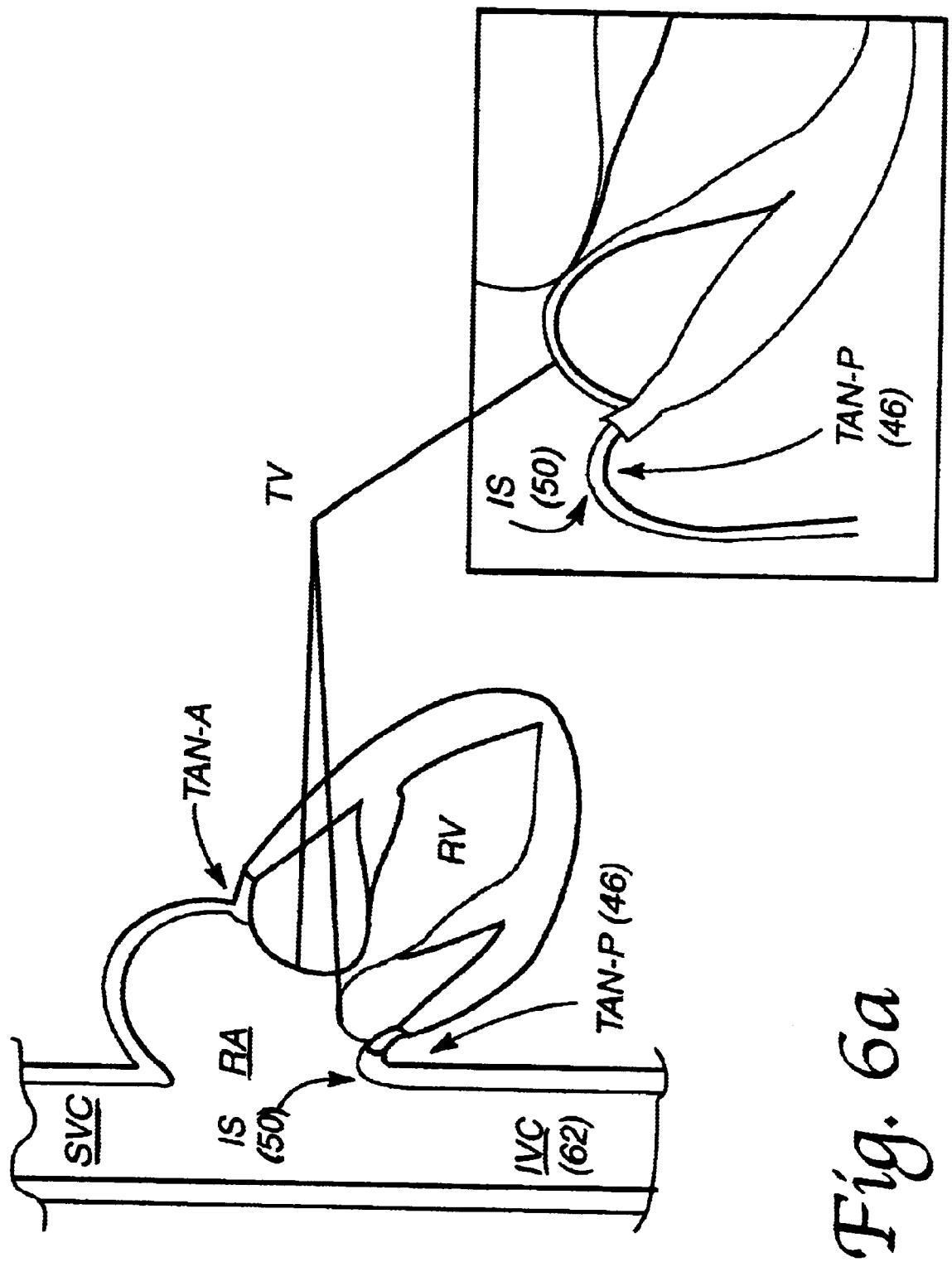
FIGS. 6a and 6b provide a diagrammatic illustration of how the catheter electrode functions in vivo.
Figure 6B:
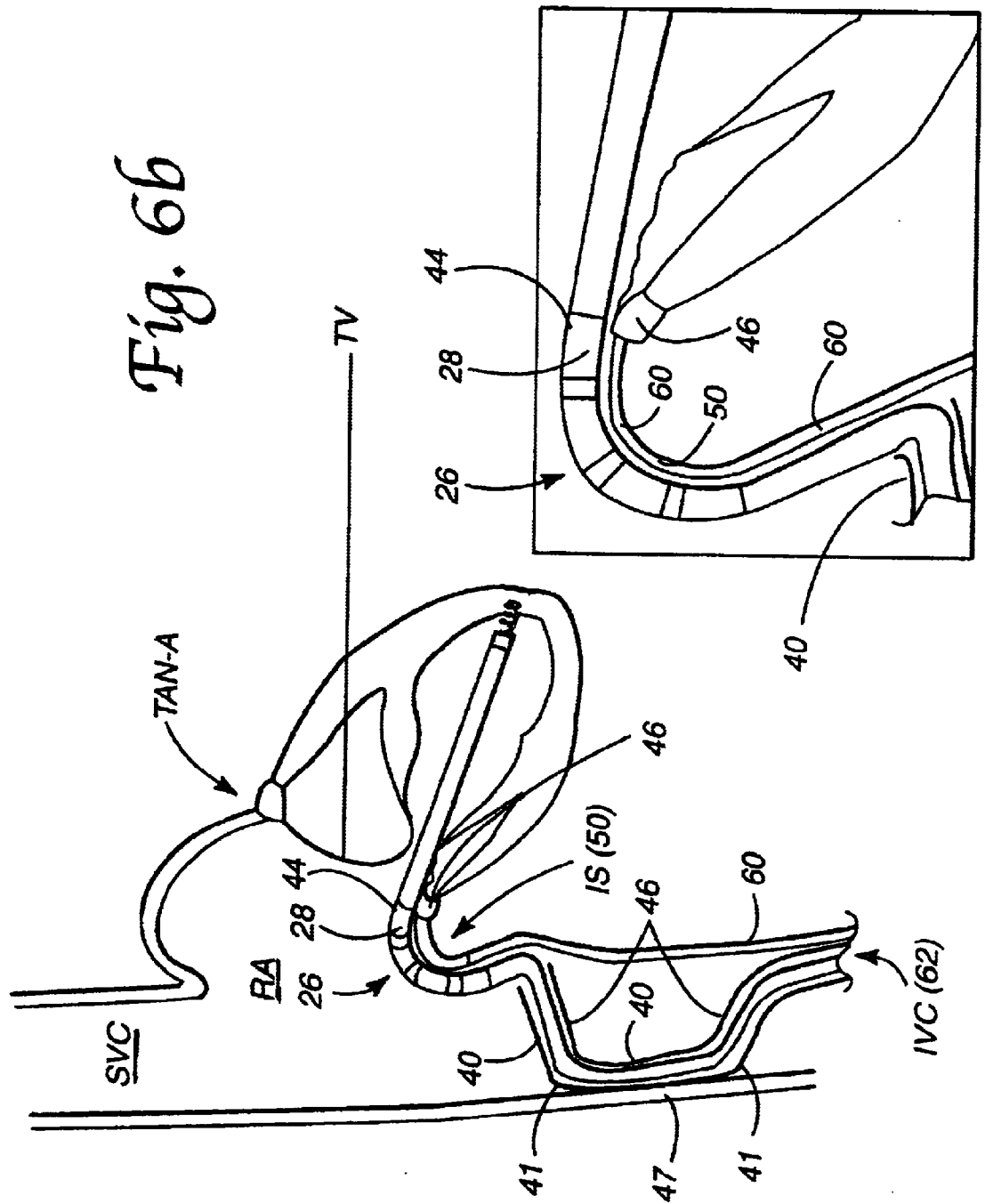

FIGS. 6a and 6b provide a diagrammatic illustration of how the catheter 10 and electrode portion 26 function in vivo in the methods of treatment of atrial flutter as provided by the invention. FIG. 6a is a longitudinal cross-sectional view of the right heart looking from the patient's right side. In these drawing figures, IVC refers to the inferior vena cava, SVC refers to the superior vena cava, RA refers to the right atrium, RV refers to the right ventricle, TV refers to the tricuspid valve (leaflet), TAN-A refers to the anterior tricuspid annulus, TAN-P refers to the posterior tricuspid annulus, and IS refers to the isthmus (between IVC inlet and TAN-P). The magnified view of isthmus area 50 is shown in the insert.

FIG. 6b, which is a similar view to FIG. 6a, illustrates how the catheter 10 and the electrode portion 26 work. The distal end 18 of the catheter 10 is anchored at right ventricular apical region with the screw-in anchoring device 16. The electrode portion 26 of the catheter 10 is placed over the isthmus 50. With a pre-shaped semirigid guiding sheath 40 creating a bend at a location proximal to the proximal end of the electrode portion 26, and with the tip of the guiding sheath 40 pointing anteriorly, the electrode portion 26 of the catheter 10 is bent to conform to the contour of the isthmus 50 and form a junction to TAN-P and IVC. By pulling down the guiding sheath 50 and the electrode portion 26, tension is created to smooth out the acute angulation of the isthmus 50 and maintain a stable contact between the ring electrodes 28 and the endocardial surface of the isthmus 50.

The foregoing description of a preferred embodiment of the catheter of the present invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A catheter for treating atrial flutter and like conditions using radio frequency energy, comprising:
    a flexible elongate tubular body having a lumen;
    at least one electrode positioned on a portion of said tubular body for supplying energy to a target area for treatment;
    an anchoring device provided at a distal end of said elongate tubular body for anchoring said tubular body at an anchoring location away from the target area such that said at least one electrode overlies the target area for treatment;
    a removable stylet positioned in said lumen for remotely controlling said anchoring device; and
    a guiding sheath for receiving said flexible elongate tubular body and having at least one bend or angulation for assisting in molding the portion of said tubular body carrying said at least one electrode for placement over the target treatment area.

2. The catheter according to claim 1, wherein said anchoring device includes a corkscrew tip for insertion in a cardiac surface for holding said flexible tubular body in place.

3. The catheter according to claim 1, wherein said guiding sheath is preshaped and said bend or angulation is shaped for assisting in molding said flexible tubular body to correspond to a contour of said treatment area.

4. The catheter according to claim 1, wherein said flexible elongate tubular body houses a metallic spring coil that provides flexibility to the catheter.

5. The catheter according to claim 4, wherein said metallic spring coil is embedded in an outer wall of said flexible tubular body.

6. The catheter according to claim 1, wherein said at least one electrode includes a plurality of spaced rings positioned along an outer surface of said flexible tubular body.

7. The catheter according to claim 6, wherein the spacing between each of said plurality of rings is about 1–2 mm, whereby said spacing permits adjacent rings to move toward or away from each other as said elongate tubular body is flexed.

8. The catheter according to claim 1, wherein said at least one electrode includes a relatively long segment of spring coil electrode.

9. The catheter according to claim 8, wherein said at least one electrode further includes an isolated ring electrode located on either side of said relatively long segment of spring coil electrode, whereby said isolated ring electrodes are useful for bipolar recording to aid in positioning said tubular body of the catheter.

10. The catheter according to claim 1, wherein said at least one electrode is positioned at least 6–16 cm from the distal end of said flexible tubular body, whereby upon anchoring said flexible tubular body in position, said at least one electrode substantially overlies the cardiac isthmus for applying radio frequency energy thereto.

11. The catheter according to claim 1, wherein said stylet includes a fitting for mating with a socket forming in a proximal end of a screw device forming a part of said anchoring device.

12. The catheter according to claim 1, wherein the shape of the flexible tubular body can be changed in vivo using the guiding sheath.

13. A catheter for treating atrial flutter and like conditions using radio frequency energy, comprising:
    a flexible elongate tubular body having a lumen;
    a flexible spring coil and at least one conductor in said tubular body;
    at least one flexible electrode positioned substantially away from a distal end of said tubular body in juxtaposition with the flexible spring coil and in electrical communication with said at least one conductor;
    an anchoring device provided at the distal end of said elongate tubular body for anchoring said tubular body in place such that said at least one electrode is positioned over a target area for treatment; and a removable stylet positioned in said lumen for remotely controlling the operation of said anchoring device, whereby the coaction of the anchoring device and the flexibility provided by said coil spring allows the at least one electrode of the catheter to be easily molded, positioned over and held in stable contact with the target area.

14. The catheter according to claim 13, further including a guiding sheath for receiving said flexible elongate tubular body and having a bend or angulation for assisting in molding a portion of said tubular body supporting said at least one electrode for positioning over the target area.

15. The catheter according to claim 13, wherein said at least one electrode includes a plurality of spaced rings positioned along an outer surface of said flexible tubular body.

16. The catheter according to claim 15, wherein said conductor comprises a plurality of wires running along said flexible tubular body and each of said plurality of spaced rings is connected to an energy source by one of said wires.

17. A catheter for treating atrial flutter and like conditions using radio frequency energy to ablate at least a portion of the cardiac isthmus, comprising:

a flexible elongate tubular body having a lumen;

at least one electrode positioned on said tubular body;

an anchoring device provided at a distal end of said elongate tubular body for anchoring said tubular body in place;

a removable stylet positioned in said lumen for remotely controlling the operation of said anchoring device; and a guiding sheath for receiving said flexible elongate tubular body and having a pre-shaped bend or angulation for molding a portion of said tubular body carrying the at least one electrode to form a curved segment for placement in contact with at least a portion of the cardiac isthmus once the anchoring device is in place.

18. The catheter according to claim 17, wherein the guiding sheath includes at least one bend or angulation for assisting in molding the catheter for placement over the cardiac isthmus.

* * * * *